United States Patent [19]

Talbot

[11] 3,989,731

[45] Nov. 2, 1976

[54] PRODUCTION OF DIMERS OF DICYCLOPENTADIENYL IRON COMPOUNDS

[75] Inventor: Meldon L. Talbot, Boulder, Colo.

[73] Assignee: Syntex Corporation, Panama, Panama

[22] Filed: Sept. 13, 1968

[21] Appl. No.: 761,015

[52] U.S. Cl. .................... 260/439 CY; 260/290 V; 260/326.81; 260/346.1 M
[51] Int. Cl.² ......................................... C07F 15/02
[58] Field of Search ............ 260/2 M, 67, 439 CY, 260/290 V, 326.81, 346.1 M; 149/19, 109

[56] References Cited

UNITED STATES PATENTS 3,341,495 9/1967 Neuse .................................. 260/67
3,849,461 11/1974 Heyer et al. .................. 260/439 CY

OTHER PUBLICATIONS

Levi, Ferrocene Polymers, U.S. Picatinny Arsenal, Dover, N. J., Plastics and Packaging Laboratory, 1966, pp. 5, 9, 13–17, and 19–21.

*Primary Examiner*—Leland A. Sebastian
*Attorney, Agent, or Firm*—Walter H. Dreger; William B. Walker

[57] ABSTRACT

Production of dimers of dicyclopentadienyl iron compounds by the reaction of a dicyclopentadienyl iron compound and a coupling agent in the presence of an acid catalyst in an organic solvent. The process involves a two-phase system wherein one phase comprises said coupling agent, a strong acid, and a polar organic solvent; and the second phase comprises said iron compound which is slightly soluble in the first phase. Dimers of dicyclopentadienyl iron compounds are excellent anti-oxidants and are also useful in controlling the rate of combustion of solid combustion mixtures.

6 Claims, No Drawings

PRODUCTION OF DIMERS OF DICYCLOPENTADIENYL IRON COMPOUNDS

This invention relates to a novel process for the production of dimers of dicyclopentadienyl iron compounds. More particularly, the present invention relates to the preparation of dimeric dicyclopentadienyl iron compounds utilizing a two-phase system.

The expression "dicyclopentadienyl iron compound", as used herein, refers to compounds having the following structure:

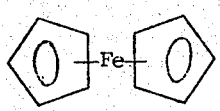

The term "ferrocene" is also used in the art to represent the above structure.

Prior to the present invention, dimers of dicyclopentadienyl iron compounds have been prepared by the reaction of a dicyclopentadienyl iron compound, specifically, ferrocene, with paraformaldehyde in concentrated sulfuric acid. Another method is to react, for example, ferrocenylmethanol and ferrocene in concentrated sulfuric acid. These and other prior art methods are disadvantageous in that the dimer product is very difficult to separate from the reaction product mixture making large scale production impractical. In addition, the foregoing prior art methods provide only low conversion of the order of 20%.

The primary object of the present invention is to provide an improved process for the production of the dimeric condensation product of a dicyclopentadienyl iron compound which overcomes the aforementioned disadvantages. Other objects, advantages, and meritorious features of the present invention will become apparent as the invention is hereinafter described in detail and from the appended claims.

Briefly stated, the process of the present invention comprises a two-phase system for the reaction of a monomeric dicyclopentadienyl iron compound with a coupling agent in the presence of a strong acid catalyst in a polar organic solvent. The acid catalyst, the coupling agent, and the polar solvent make up one phase of the system and the dicyclopentadienyl iron compound makes up the second phase of the system, said iron compound being slightly soluble in said first phase. By using the two-phase system of the present invention, an excellent yield of the dimeric condensation product is obtained. In addition, recovery problems of the dimeric product are minimized in that the dimeric product is essentially insoluble in the first phase of the system. Further, the strong acid catalyst and the polar organic solvent can be reused several times which reduces chemical disposal problems and makes for a more economical process.

In the practice of the process of the present invention, there is first prepared a mixture of the polar organic solvent and the acid catalyst. Generally, the addition of the acid to the organic solvent requires the use of external cooling. The particular strong acid used is not critical and can be either an organic or inorganic acid, such as sulfuric acid, phosphoric acid, p-toluenesulfonic acid, hydrochloric acid, and the like. The acid can be of either technical or research grade or of higher purity. The organic solvent employed is not critical so long as the combination of the acid and organic solvent is substantially insoluble in the monomeric dicyclopentadienyl iron compound. As a guide, the organic solvent should be selected from polar organic solvents such as lower saturated aliphatic alcohols, e.g., methanol, ethanol, isopropanol, or n-butanol and mixtures thereof, e.g., methanol, ethanol, or other polar organic solvents, such as acetonitrile. The mixture of the acid and polar organic solvent can also contain water, i.e. it need not be an anhydrous mixture. It is preferable, however, to keep the water content of the acid-organic solvent mixture at below about 50% by weight of the mixture. The amount of strong acid can vary considerably. In the practice of the process, there is generally used from about one to five molar equivalents of acid based on the amount of dicyclopentadienyl iron compound. There is generally no advantage in using more than five molar equivalents.

To the mixture of the acid catalyst and the polar organic solvent there is added dicyclopentadienyl iron compound. The addition of the dicyclopentadienyl iron compound results in the formation of a two-phase system by reason of the slight solubility of the iron compound in the acid-polar organic solvent mixture. The amount of dicyclopentadienyl iron compound employed in generally at least two molar equivalents based on the amount of coupling agent to be added. An amount greater than two molar equivalents can be used but is generally unnecessary. In those instances where the dicyclopentadienyl iron compound is a solid material, it is preferable to form a solution of the iron compound in an organic solvent prior to addition to the acid-polar organic solvent mixture. The organic solvent used to dissolve the iron compound should be only slightly soluble in the acid-polar organic solvent mixture. As a guide, there can be used non-polar organic solvents, such as benzene, toluene, xylene, pentane, and the like.

There is next added a coupling agent which is soluble in the acid-polar organic solvent mixture. The particular coupling agent employed is not critical so long as it is a coupling agent which is soluble in the acid-solvent mixture and which, in the presence of strong acid, generates a lower alkylene radical to bridge the monomeric dicyclopentadienyl iron compound to form the dimeric product. Formaldehyde (formalin), paraformaldehyde, methylal, s-trioxane, and chloromethylmethyl ether are exemplary of coupling agents which can be used in the practice of the present invention. The addition of the coupling agent to the two-phase system is preferably accomplished at a relatively slow rate and with stirring or other agitation means. When the coupling agent is added at a fast rate, unreacted coupling agent may accumulate which can react with dimeric product to form trimeric or polymeric products. Thus, to minimize formation of trimers and polymers, the coupling agent is added at a relatively slow rate with agitation and at an elevated temperature. Although the reaction can be carried out at room temperature, it is preferable to first heat the two-phase system to above room temperature, for example, about 55° C to the reflux temperature of the system, and then add the coupling agent at a relatively slow rate while maintaining an elevated temperature, e.g., the reflux temperature. Upon completion of the addition of the coupling agent, heating of the reaction mixture is continued until the reaction is complete as followed by the ratio of dimer product to unreacted monomer as determined by, for example, vapor phase chromatography.

The reaction is generally complete in from about 0.5 hours to 4 hours, the optimum time being dependent upon the particular cyclopentadienyl iron compound used, efficiency of stirring, rate of addition of the coupling agent, size of batch and temperature. The most optimum temperature, reaction time and rate of addition of the coupling agent for a particular dicyclopentadienyl iron compound and coupling agent is easily determinable by one of ordinary skill in the art giving due consideration to the foregoing factors.

Upon completion of the reaction, the dimeric product is easily separated from the reaction mixture due to its relative insolubility with the first phase of the system. Hence, the dimeric product can be separated, for example, simply by decanting and thereafter, depending upon the degree of purity sought, can be further purified by, for example, distillation to distill off the lower boiling monomeric iron compound and any nonpolar solvent which may have been used. The remaining acid-organic solvent mixture following this separation can be reused several times, e.g., four or five times with good results.

Dicyclopentadienyl iron compounds are also referred to in the literature as ferrocene and ferrocene derivatives. The process of the present invention can be used for the formation of a dimeric condensation product of dicyclopentadienyl iron compounds in general. For example, the dicyclopentadienyl iron compounds or ferrocene derivatives of Formula I:

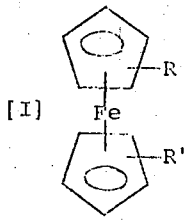

[I]

wherein each of R and R', independent of the other, is hydrogen, alkyl, cycloalkyl, aryl, or heterocyclic. Dicyclopentadienyl iron compounds can be prepared as described in U.S. Pat. Nos. 2,680,756; 2,791,597; 2,804,468; 2,834,796; 3,092,647; 3,285,946; 3,294,685; 3,382,268; and 3,383,314. Specific examples of compounds of Formula I are dicyclopentadienyl iron (ferrocene), di(methylcyclopentadienyl)iron, di(ethylcyclopentadienyl)iron, methylferrocene, ethylferrocene, n-butylferrocene, dihexylferrocene, phenylferrocene, m-tolyferrocene, didecylferrocene, dicyclohexylferrocene, and dicyclopentylferrocene.

The term "alkyl" refers to an alkyl group, branched or straight chain, of one to ten carbon atoms, such as methyl, ethyl, propyl, n-butyl, hexyl, or heptyl. The term "cycloalkyl" refers to a lower cycloalkyl group of three to seven carbon atoms, such as cyclopentyl or cyclohexyl. The term "aryl" refers to an organic radical derived from an aromatic compound by the removal of one hydrogen atom, e.g., phenyl and substituted phenyl, such as lower alkyl substituted phenyl, e.g., tolyl, ethylphenyl, triethylphenyl, halophenyl, e.g., chlorophenyl, or nitrophenyl, e.g., p-nitrophenyl. The term "heterocyclic" refers to pyrryl, pyridyl, furfuryl, and the like. Although any aryl or heterocyclic substituted dicyclopentadienyl iron compound can be used, the aryl or heterocyclic group generally contains up to about 15 carbon atoms.

The dimeric products (including isomeric mixtures) prepared by the process of the present invention are useful as anti-oxidants, e.g., in polymers, such as polyethylene, SBR, natural rubber, and the like. The dimeric products (including isomeric mixtures) are also useful as catalysts for the control of the rate of burning of solid combustion mixtures, such as solid rocket propellant mixtures. They can be used in solid propellant mixtures in the same way as ferrocene. The dimeric products prepared by the process of the present invention are less prone to migration within the propellant mixture than is ferrocene. Thus, a solid propellant mixture containing the catalyst can be stored for long periods of time without fear of the catalyst migrating during storage.

The process of the present invention, which has been discussed hereinabove in respect to formation of dimer products, can also be advantageously used for the production of trimeric and tetrameric products. The formation of trimers and tetramers is favored by choosing a solvent in the first phase of the system in which the monomeric iron compound is more soluble, ie. a less polar solvent and/or by reversing the addition of the coupling agent and dicyclopentadienyl iron compound.

The following examples are provided to illustrate the practice of the present invention. All proportions, unless otherwise stated, are by weight and temperature in degrees centigrade.

EXAMPLE 1

A mixture of 207 parts of methyl alcohol and 196 parts of conc. sulfuric acid (reagent grade) is prepared, under nitrogen, maintaining the temperature below about 50° C. To this mixture is rapidly added 242 parts of n-butylferrocene. The resulting mixture is heated to reflux and 42 parts of methylal is added dropwise with stirring. The reaction mixture is refluxed for a total of 3 hours including the time required for addition of the methylal. The reaction mixture is allowed to cool and 130 parts of Skellysolve C [a mixture of hydrocarbons having an sp. gr. (60° F) 0.726, Aniline point 130.2° F and Kauri butanol value 36.2]is added. The organic layer is separated and a small amount of sodium carbonate (20 parts) and absorptive magnesium silicate (3 parts) added and the mixture filtered. The filtrate is distilled until unreacted n-butylferrocene is removed to provide dimeric n-butylferrocene having a viscosity of 161 centistokes (Cannon-Fenske method at 100° F), in 94% yield which corresponds to 62% conversion.

The process of Example 1 can be schematically represented as follows:

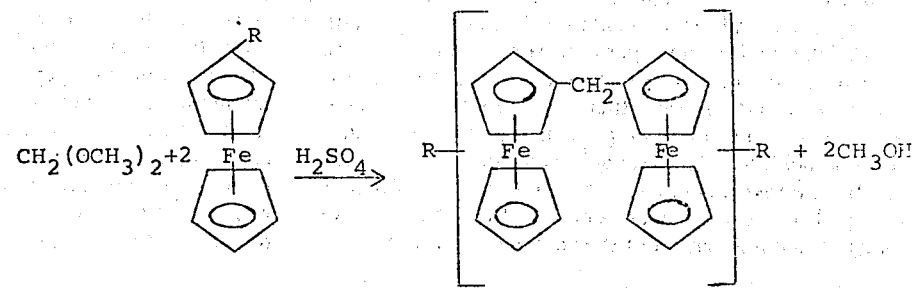

wherein R represents n-butyl.

EXAMPLE 2

Into a nitrogen purged reflux vessel containing 38.8 parts methyl alcohol, there is added, under nitrogen atmosphere, 36.7 parts sulfuric acid (66° Baume) holding the temperature below 50°. To this mixture is rapidly added 45.4 parts n-butylferrocene. The resulting mixture is heated to reflux and 7.5 parts methylal is added without letting the reaction temperature drop below about 77°. The reaction mixture is refluxed with stirring for a total of 3 hours which includes the time used for adding methylal. The reaction mixture is cooled and allowed to settle. The organic layer is drawn off leaving the sulfuric acid-methanol phase for reuse.

The remaining sulfuric acid-methanol solution is heated to 85°–90° and then 45.4 parts of n-butylferrocene is added rapidly. This mixture is heated to reflux and 7.5 parts of methylal added without letting the temperature drop below about 77°. The reaction mixture is heated for a total of 3 hours as before and then cooled and allowed to settle. The organic layer is drawn off leaving the sulfuric acid-methanol phase for reuse.

The recycle procedure of the preceding paragraph is repeated two more times and the organic layer of all four cycles combined. To the combined organic layer is added 108 parts Skellysolve C, 15 parts sodium carbonate, and 2.2 parts absorptive magnesium silicate. The mixture is stirred, filtered, and the filter washed 3 × 12 parts Skellysolve C. The filtrate is distilled to remove unreacted n-butylferrocene to yield dimeric n-butylferrocene having a viscosity of 148 centistokes (Cannon-Fenske method at 100° F).

EXAMPLE 3

The process of Example 1 is repeated with the exception that methanol is replaced with an equal amount of ethanol/methanol (1:1) with equally good results.

By using an equivalent amount of chloromethyl-methyl ether in place of methylal in the process of Example 1, there is similarly obtained the dimeric condensation product of n-butylferrocene.

EXAMPLE 4

A mixture of 207 parts methyl alcohol and 196 parts conc. Sulfuric acid is prepared, under nitrogen, while maintaining the temperature below 50°. Ethylferrocene (214 parts) is added and the mixture heated to 65°. Methylal (42 parts) is added slowly with rapid stirring while maintaining the temperature at about 65° (total addition time of about 45–60 minutes). Stirring is continued at about 65° for a total time of 5 hours. Heating and stirring is discontinued and the reaction mixture allowed to stand. The bottom organic layer is removed and to it is added 200 parts Skellysolve C, 20 parts sodium carbonate, and 3 parts absorptive magnesium silicate. The resulting mixture is stirred and then filtered at room temperature. The filtrate is distilled to remove Skellysolve C and unreacted ethylferrocene to yield dimeric ethylferrocene (containing 5% or less unreacted ethylferrocene) in 90% yield (63% conversion) having a viscosity of 150 centistokes (Cannon-Fenske Method at 100° F). The dimeric ethylferrocene product is placed under nitrogen for storage.

EXAMPLE 5

The process of Example 1 is repeated with the exception that n-heptane is used in place of Skellysolve C with equally good results.

What is claimed is:

1. In the process for the production of dimeric condensation product of a dicyclopentadienyl iron compound involving the reaction of a dicyclopentadienyl iron compound selected from those of the following formula:

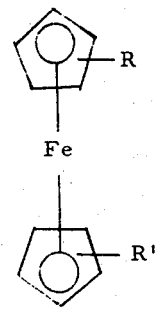

in which each of R and R' is hydrogen, alkyl, cycloalkyl, monocyclic aryl, pyrryl, pyridyl, or furfuryl, with a methylene radical generating coupling agent selected from the group consisting of formaldehyde, paraformaldehyde, methylal, s-trioxane, and chloromethylmethyl ether in the presence of a strong acid catalyst, the improvement wherein said iron compound and said coupling agent are reacted at a temperature of between room temperature and reflux temperature in a two-phase system wherein the first phase comprises said strong acid and a polar organic solvent and the second phase comprises said iron compound, said coupling agent being added slowly to the two-phase system with agitation, said second phase being slightly soluble in said first phase.

2. The process according to claim 1 wherein each of R and R' is hydrogen or alkyl.

3. The process according to claim 1 wherein the polar organic solvent is a lower saturated aliphatic alcohol, the strong acid is an inorganic acid and each of R and R' is hydrogen or alkyl.

4. The process according to claim 1 wherein the polar organic solvent is methanol, ethanol or mixture thereof, the acid is sulfuric acid, each of R and R' is hydrogen or alkyl and the reaction temperature is about reflux temperature.

5. The process according to claim 1 wherein the polar organic solvent is methanol, ethanol or mixture thereof, the acid is sulfuric acid, the iron compound in n-butylferrocene, the coupling agent is methylal and the reaction temperature is about reflux temperature.

6. The process according to claim 5 wherein the polar organic solvent is methanol.

* * * * *